Jan. 1, 1957 E. S. BOERNER Plant Pat. 1,548
CHRYSANTHEMUM PLANT
Filed Feb. 27, 1956
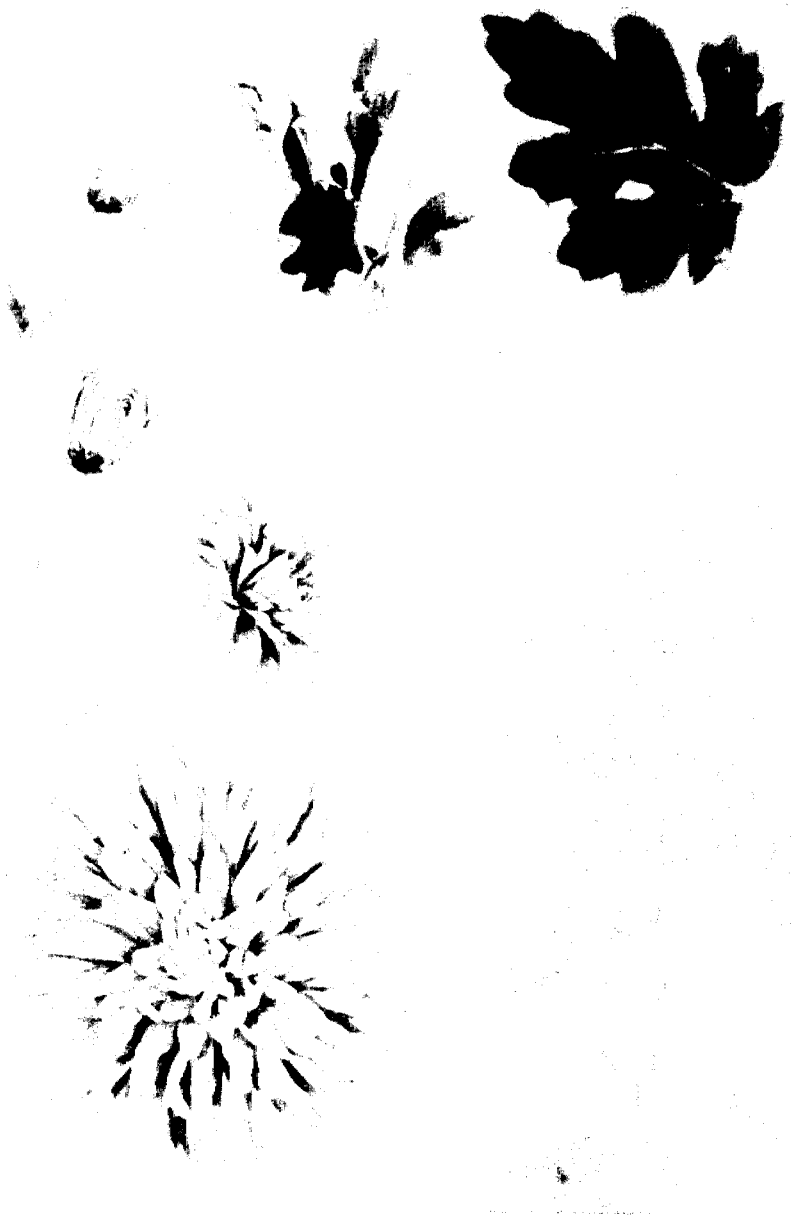
Inventor.
E. S. Boerner
By: Robb & Robb
Attorneys.

United States Patent Office

Plant Pat. 1,548
Patented Jan. 1, 1957

1,548

CHRYSANTHEMUM PLANT

Eugene S. Boerner, Newark, N. Y., assignor to Jackson & Perkins Company, Newark, N. Y., a corporation of New York Application February 27, 1956, Serial No. 568,129

1 Claim. (Cl. 47—60)

The present invention relates to a new and distinct variety of chrysanthemum plant of the decorative type, which was originated by me by crossing the variety "Tanager" (Plant Patent No. 1129) with the variety "Kingbird" (Plant Patent No. 1306).

The primary objective in making this cross was to produce a new chrysanthemum variety generally similar to "Kingbird," including the characteristic hardiness of the latter, but which bears flowers of a different color. This objective was fully achieved, along with other advantages and improvements, as evidenced by the fact that the new variety is hardy; has glossy Dark Green foliage; bears distinctive flowers which are Pomegranate Purple, lightly overcast with Spinel Red, in general color tonality; and the new variety is freely reproducible by suckers, which is unusual for a chrysanthemum in this color.

The foregoing characteristics and distinctions differentiate my new variety from its parents, as well as from all other varieties of its class of which I am aware, and asexual reproduction of the new variety by both top cuttings and underground runners, as performed by me at Newark, New York, shows that these characteristics and distinctions come true to form and are established and transmissible through succeeding propagations.

The accompanying drawing shows typical specimens of the vegetative growth and flowers of the new variety in different stages of development and as depicted in color as nearly true as it is reasonably possible to make the same in a color illustration of this character, as well as a typical plant specimen which is depicted in black-and-white and shows the upright, compact and free habit of growth of the plant.

The following is a detailed description of my new variety, with color terminology in accordance with Ridgway's Color Standards and Nomenclature:

Parentage: "Tanager" × "Kingbird."
Classification: Decorative type.
Growth: Vigorous; from 25 to 30 inches tall.

Cold Resistance: Winter hardy in Northern New York; flowers show no frost burn with early frosts.
Blooming Period: In the Newark, New York, climatic area, blooming begins about October 15th and continues until heavy frosts.

FLOWER (Observations made from specimens grown in a field at Newark, New York, in the middle of October, and in the early morning.)

Bud:
- *Color.*—When sepals first divide—Indian Lake, Plate 26. When petals begin to unfurl—Pomegranate Purple, Plate 12. When half-blown: Inside of petals—Eugenia Red, Plate 13; outside of petals—Rocellin Purple, Plate 38, lightly overcast with Light Vinaceous-Fawn, Plate 40.
- *Peduncle.*—Strong. Color—Light Elm Green, Plate 17.

Bloom:
- *Size.*—From 4 inches to 4½ inches.
- *Stem.*—Short; strong.
- *Form.*—Decorative.
- *Petalage.*—Double; wide.
- *Color.*—Center of flower—Spinel Red, Plate 26, lightly overcast with Eugenia Red, Plate 13. Outer petals—Pomegranate Purple, Plate 12. Base of petals—Clear Dull Green-Yellow, Plate 17. Inside of petals—Pomegranate Purple, Plate 12, lightly overcast with Spinel Red, Plate 26. Reverse of petals—Light Ochraceous Salmon, Plate 15, lightly overcast with Eugenia Red, Plate 13.
- *Petals.*—Texture—medium. Form—oval.
- *Fragrance.*—Characteristic chysanthemum.

PLANT

Form: Upright; compact.
Growth: Free; many suckers.
Foliage:
- *Size.*—Medium.
- *Quantity.*—Heavy.
- *Color.*—Upper side—Varley's Green, Plate 18; reverse side—Cress Green, Plate 31.
- *Texture.*—Leathery; glossy.

I claim:

A new and distinct variety of chrysanthemum plant of the decorative type, substantially as herein shown and described, characterized particularly as to novelty by its hardiness, glossy Dark Green foliage, the Pomegranate Purple lightly overcast with Spinel Red general color tonality of its flowers, and the unusual freedom of its reproduction by suckers.

No references cited.